United States Patent [19]

Wang

[11] Patent Number: 5,034,420
[45] Date of Patent: Jul. 23, 1991

[54] COMPOSITIONS AND METHOD FOR STABILIZATION OF ANTHRALIN COMPRISING THE ADDITION OF AN OIL SOLUBLE ANTIOXIDANT AND AN ANIONIC SURFACTANT

[75] Inventor: Jonas C. T. Wang, East Amherst, N.Y.

[73] Assignee: Bristol-Myers Squibb Co., New York, N.Y.

[21] Appl. No.: 361,458

[22] Filed: May 17, 1989

Related U.S. Application Data

[60] Division of Ser. No. 871,959, Jun. 9, 1986, abandoned, which is a continuation of Ser. No. 706,438, Feb. 27, 1985, abandoned, which is a continuation of Ser. No. 502,852, Jun. 9, 1983, abandoned.

[51] Int. Cl.$^5$ .................. A61K 31/12; A61K 31/10; A61K 31/05
[52] U.S. Cl. .................. 514/680; 514/711; 514/732; 514/973
[58] Field of Search ............ 514/680, 732, 711, 973

[56] References Cited

U.S. PATENT DOCUMENTS

| 3,881,000 | 4/1975 | Friedmann et al. | 514/105 |
| 3,924,004 | 12/1975 | Chang et al. | 514/772 |
| 4,137,302 | 1/1979 | Humbert et al. | 424/47 |
| 4,203,969 | 5/1980 | Yarrow et al. | 424/83 |
| 4,287,214 | 9/1981 | VanScott et al. | 514/732 |
| 4,551,480 | 11/1985 | Stiefel et al. | 514/680 |

OTHER PUBLICATIONS

The Journal of Pharmaceutical Sciences, 70, 1205-7 (1981), J-C Caron et al.

Primary Examiner—Richard L. Raymond
Assistant Examiner—Gary E. Hollinden
Attorney, Agent, or Firm—Sandra M. Nolan

[57] ABSTRACT

This invention relates to an anthralin composition having improved stability. The invention further relates to a method for increasing the stability of anthralin in dermatological compositions by incorporating therein a stability enhancing amount of an acid stable anionic surfactant and a water soluble antioxidant.

21 Claims, 1 Drawing Sheet

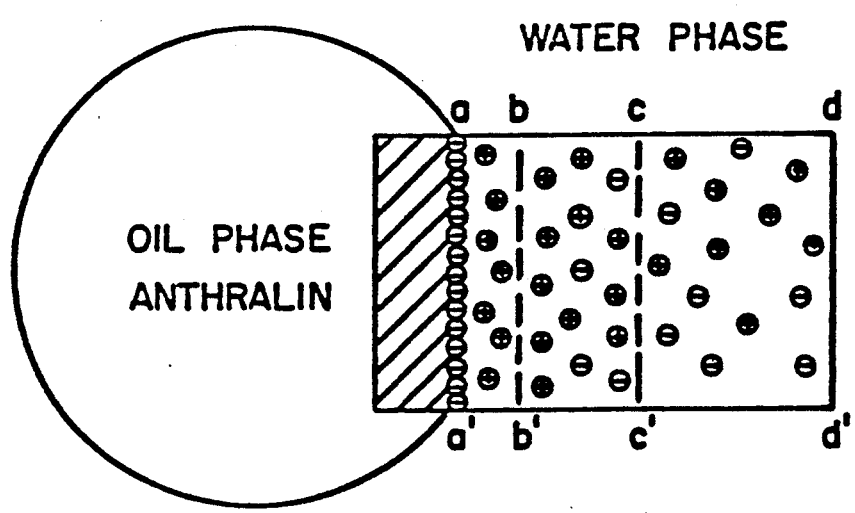

COMPOSITIONS AND METHOD FOR STABILIZATION OF ANTHRALIN COMPRISING THE ADDITION OF AN OIL SOLUBLE ANTIOXIDANT AND AN ANIONIC SURFACTANT

This application is a continuation-in-part of Ser. No. 871,959, filed June 9, 1986 (now abandoned), which was a continuation-in-part of Ser. No. 706,438, filed Feb. 27, 1985 (now abandoned), which was a continuation-in-part of Ser. No. 502,852, filed June 9, 1983 (now abandoned).

Anthralin, also known as dithranol, has been a common component in formulations used in the percutaneous treatment of psoriasis, a dermatological affliction characterized by thickened, reddened, silvery scale-like patches of skin that may appear as a few small lesions or may cover large areas of the body.

Although dermatologists, in recent years, have used a number of newer approaches in treating psoriasis, the large number of therapeutic agents and regimens employed attest to the lack of sustained efficacy of the majority of the same. The treatment of psoriasis has involved the use of a wide variety of topical medications, for example, tars, tar derivatives, anthralin, mercury compounds, corticosteroids and keratolytics.

Anthralin still remains the treatment of choice for many dermatologists treating psoriasis. In general anthralin is employed as a "main line" in-patient and out-patient treatment in most hospitals. For such purpose, the anthralin is generally employed in concentrations ranging from 0.05% to 5% by weight based on the total weight of the composition. Unless otherwise stated, as used hereinafter, percent by weight means percent by weight based on the total weight of the composition. When properly used anthralin is extremely efficacious, and its use is accompanied by minimal to no adverse reactions.

Even though anthralin is generally recognized to be highly efficacious in the treatment of psoriasis, it still suffers from three major drawbacks: instability, staining of the skin and clothing, and skin irritation. Anthralin undergoes light-catalyzed oxidation, dimerization and/or chemical decomposition whereby 1,8-dihydroxyanthraquinone and 1,8,1',8'-tetrahydroxy-10,10'-dianthrone and other unidentified side products are produced.

Anthralin has been disclosed to be susceptible to auto-oxidation degradation (viz. free radical oxidation). Its degradation products are believed to be inactive in the chemotherapy of psoriasis. The "irritation" or "anthralin erythema" of skin is believed to be primarily caused by the initial free radical intermediates of anthralin. The "staining" of skin by anthralin is believed to be attributable to its oxidation products viz. 1,8-dihydroxy anthraquinone or the dimer.

Many solutions to the anthralin stability problem have been reported in the prior art, but none have been sufficiently satisfactory. Typical of the prior art solutions are those disclosed in U.S. Pat. Nos. 4,203,969 and 4,287,214. U.S. Pat. No. 4,203,969 discloses criticality in the use of a water soluble, oil insoluble acid antioxidant or a combination of an acid and a water soluble, oil insoluble antioxidant in the continuous aqueous phase of a cream. U.S. Pat. No. 4,287,214 discloses that antioxidants, such as ascorbic acid, BHA (butylated hydroxyanisole) and BHT (butylated hydroxytoluene) and other chemicals, such as salicylic acid, do not satisfactorily stabilize anthralin whereas, certain alpha hydroxy acids do. Ponce-Waelsch and Hulsebosch, Arch. Derm. Forsch. 249, 141–152 (1974) disclose a Lactacyd pH2 ® cream vehicle containing anthralin. Table 1 of that reference demonstrates the lack of stability of such a formulation when analyzed by UV spectroscopy and thin layer chromatography. Although, Caron and Shroot, J. Pharm. Sci. 70:11, 1205–1207 (1981) disclose salicylic acid in a 0.44% anthralin containing composition which also contains cetyl alcohol, sodium lauryl sulfate, paraffin and petrolatum, in fact there is no clear disclosure that the composition contains any water nor is there any appreciation of any anthralin stabilizing effect provided by any of the components of the composition or the concentration ranges in which such components could be employed in providing a stable water and anthralin containing composition at effective antipsoriatic levels.

When anthralin stability is determined by use of high pressure liquid chromotography (HPLC) using the method described in Caron et al., J. Pharm. Sci. 70:11, 1205 (1981) or that described in Pharmacopeial Forum, May–June 1982, pgs. 1956–1957; The United States Pharmacopeial Convention, Inc., instead of the more commonly used United States Pharmacopeia (USP) method of determining stability, it is found that the prior art methods for stabilizing anthralin are not completely satisfactory, generally providing less stability than heretofore thought to be provided. In contrast to the USP method, which is less than satisfactory for determining anthralin stability, the HPLC method is a selective, sensitive and reproducible method for determining anthralin stability. Recent publications, such as heretofore referred to, have raised serious questions as to whether in fact USP and British Pharmacopeia (BP) methods are anthralin stability indicating. It is expected that the USP and the BP will shortly change their assay method to HPLC for all anthralin containing formulations.

For most commercial applications, concentrations of anthralin greater than 0.5% weight are seldom, if ever, marketed for out-patient application, as such compositions incur rapid loss of activity and oxidation of the anthralin. Where plaque psoriasis affected more than 20% of the body surface area, in-patient hospital treatment was necessary to avoid irritation to normal skin in contact with the higher concentration anthralin formulations and control the stability of the product while providing rapid treatment. One major shortcoming of low concentration formulations, i.e., about 0.5% or less, is that it is impossible to provide for the rapid treatment possible with formulations containing higher concentrations of anthralin.

Evidence in the prior art indicates that:

a. Anthralin is susceptible to auto-oxidation degradation (free radical oxidation), and its degradation products are inactive in chemotherapy of psoriasis;

b. The irritation or anthralin erythema of skin is mostly caused by the initial biologically active free radical intermediates of anthralin;

c. The staining of skin and clothing by anthralin is due to its oxidation products, such as its colored dimer or 1,8-dihydroxy anthraquinone.

Prior art attempts to stabilize anthralin against oxidation included the traditional prevention methods, such as the use of ascorbic acid, BHA, BHT, EDTA (ethylenediamine tetracetic acid), citric acid, adjustment of pH to an acidic pH, reduction of process temperature, removal of peroxides and protection from light. However, none of the foregoing attempts to stabilize anthralin as described in the prior art has been adequate.

It is clear from the above that the anthralin degradation products or the initial free radical intermediates cause the irritation and staining problem heretofore thought to be an unavoidable incident of anthralin therapy. If anthralin stability could be improved, the irritation and staining problems indirectly caused by anthralin degradation products would be solved concomitantly.

Even though new formulations of anthralin products have been developed for better patient tolerance, more convenience and less discoloration, the instability of anthralin in such formulations, as manifested by loss of activity and a change in color from light yellow to brown, to black, has heretofore remained an unresolved problem. No anthralin formulation has yet been made available that will afford long term stability of the anthralin per se and physical stability of the formulation coupled with an attractive appearance and an acceptable color. It is well known that commercially available anthralin products discolor in a short period of time with a resultant appearance that is highly unattractive and unacceptable to the end user.

It has now been discovered that the desired stabilization of anthralin in compositions suitable for topical application in the treatment of psoriasis can be attained by adding an anthralin stabilizing amount of an acid stable, water soluble anionic surfactant to a composition containing water, anthralin and an oil soluble antioxidant, and having a pH of 5.3 or less, such composition optionally containing, in addition, a water soluble antioxidant in the aqueous phase. The presence of a water soluble antioxidant in the aqueous phase has now been found, contrary to the teachings of U.S. Pat. No. 4,203,969, not to be critical to the long term stability of anthralin in formulations of the present invention. Although it is not critical, the presence of a water soluble antioxidant may be desirable.

Preferably, the anthralin employed in the present invention will be in a concentration of up to about 5.0% by weight. More preferably, about 0.1% to about 3.0% by weight anthralin may be employed in compositions suitable for topical application and most preferably, about 0.5% to 2.0% by weight may be employed.

Of course, higher concentrations of anthralin can also be stabilized by means of the present invention, but care must be exercised in the use of such compositions to avoid irritation to normal skin.

The anionic surfactant is used in an amount sufficient to stabilize the anthralin. Preferably, the anionic surfactant is employed at a level of 0.05% to 10% by weight, more preferably 0.1% to 5.0% by weight, and most preferably 0.3% to 1.0% by weight.

Although it is known from the prior art that anthralin is more stable at an acidic pH and that the pH of anthralin containing compositions may be controlled by the use of any dermatologically acceptable acid, it is preferred to employ an acid such as citric of salicylic acid. The pH of anthralin containing compositions containing an acid stable, water soluble anionic surfactant in accordance with the present invention is at a pH of 5.3 and below. It is preferred that lower pH's be employed, the limiting factor being skin irritation. Preferably, a pH below 4.0 is employed and more preferably a pH below 3.4.

The present invention provides an anthralin product having long term anthralin stability, cosmetic elegance, better patient tolerance and having substantially no discoloration after storage when packaged appropriately. It may be used successfully in both low strength, long term out-patient treatment and in high strength, short term in-patient or out-patient treatment of psoriasis.

It is hypothesized that the present invention may work because particles or drops of oil dispersed in liquid media may become charged in one of two ways. The first way involves the reaction adsorption of particular ions present in solution. In case of water, it may be the hydronium or the hydroxyl ion. The majority of particles or drops of oil dispersed in a water media acquire a negative charge due to preferential adsorption of the hydroxyl ion. The second way involves charges on particles or drops of oil, where the charges arise from the ionization of functional groups of surface active agents, e.g., the phosphates, carboxylates, sulfates and the sulfonates which may be situated at the surface of the particle or the interface of the oil-water phases.

Molecules and ions that are adsorbed at surfaces or interfaces are termed surface active agents or surfactants. An alternative expression is amphiphile, which suggests that the molecule or ion has a certain affinity for both polar and nonpolar solvents. It is the amphiphilic nature of surface active molecules or ions which causes them to be adsorbed at the interface, which may be liquid/gas or liquid/liquid.

The chemical structure of anthralin is shown as:

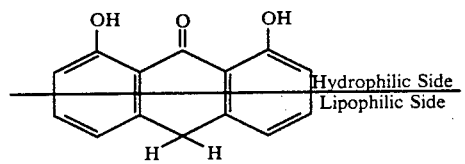

Anthralin is an amphiphile-type molecule; in other words, the anthralin has a certain affinity for both polar and nonpolar groups. The amphiphile nature of anthralin molecules also causes them to concentrate at the surface or interface where they are subject to easy attack. Under such conditions, oxidation initiators, such as oxygen, light, hydrogen ions or metal ions, will easily attack the anthralin and/or accelerate its degradation through free radical auto-oxidation. High surface or interface concentration of anthralin molecules also accelerates dimer formation because of the intramolecular interaction.

It is hypothesized that the present invention creates particles, drops of oil or micelles, the surface of which contains a mostly anionic charge created by either the sole anionic surfactant or the combination of non-ionic surfactant(s) with anionic surfactant(s). The negatively charged surface is provided by the functional groups, e.g. sulfonates, sulfates, phosphates, carboxylates, etc. of the anionic surface active agent(s). The anionic groups of acid stable surface active agents are adsorbed onto the surface at the oil/water interface, providing a negatively charged surface to the oil particle, drop or micelle. Cations in the aqueous phase will be attracted to the negatively charged surface, which also repels any anions in the solution, such as hydroxyl, once the initial adsorption is complete. In addition to these electrical forces, thermal motion tends to produce an equal distribution of all the ions in solution. As a result, an equilibrium situation is created and the system as a whole is electrically neutral.

The partition ratio of anthralin between oil and water is in favor of the oleaginous phase to the extent of approximately between 5,000 to 10,000 to 1. Therefore, in the case of oil-in-water emulsion based preparations, e.g., creams, gels, etc., or emulsified ointment, the anthralin molecules are dissolved in and are virtually retained by the oil-phase. Once the initial adsorption at the surface is complete, the surface area is occupied by anionic and/or non-ionic surfactant molecules. The anthralin molecules will not be concentrated at the surfaces and are fully protected by the negatively charged surface which repels the approach of hydroxyl ions or other degradation initiators.

Such a situation can be described by the diagram appearing in the drawing as FIG. 1, wherein the anthralin molecules are retained in the oil-phase and line a,a' is the surface of the particle, oil-drop or micelle. The adsorbed ions which give the surface its negative charge are referred to as potential determining ions and come from the anionic surfactant(s). Immediately adjacent to this surface layer is a region of tightly bound molecules of the continuous water phase together with some positive ions, mostly hydronium ions also tightly bound to the surface. The limit of this region is given by the line b,b'. The potential at line b,b' is still negative but there are less cations than at the bound negative layer. In the region bounded by the lines b,b' and c,c' there is an excess of negative ions. Beyond line c,c', the distribution of ions is uniform and electrical neutrality is obtained. Line d,d' shows the outer limit.

The anionic surfactant(s) used as a stabilizer for anthralin compositions in accordance with the present invention produces a dramatic increase in the stability of anthralin. It is believed that the anionic surfactant(s) protects anthralin molecules from attack by creating a negatively charged surface which forms micelles or by surface separation. Although the anionic surfactant(s), when employed in an anthralin stabilizing amount, will provide the advantages of the present invention, as mentioned heretofore, stabilization can be further enhanced through the use of antioxidants which have been used in the past in anthralin containing compositions.

The acid stable, water soluble, anionic surfactants used in the present invention are readily available compounds, typically selected from such non-soap surfactants as alkyl sulfates, alkyl sulfonates, alkyl benzene sulfonates, alpha sulfonyl fatty acids, alkyl phosphates, dioctyl sulfosuccinate, isethionates, alkyl ether sulfates, methyl sarcosines and the like. Preferably employed are sodium lauryl sulfate, sodium octoxynol-3-sulfonate, sodium dodecyl benzene sulfonate, sodium lauryl sulfonate, DEA oleth-3-phosphate, sodium dioctyl sulfosuccinate, sodium cocyl isothionate, sodium laureth sulfate and sodium lauryl sarcosinate and the like. Mixtures of such surfactants may also be employed.

Contrary to the teachings of the prior art, the compositions of the present invention offer long term stability without water soluble antioxidants although they may be added for enhanced results.

It has been further found that the anionic surfactants of the present invention, when used in combination with oil soluble antioxidants dramatically increase anthralin stability. Typical of such antioxidants are ascorbyl palmitate, hydroquinone, propyl gallate, nordihydroguaiaretic acid, BHT, BHA, alpha tocopherol, phenyl alpha napthylamine and lecithin. It has also been found that water soluble antioxidants may be additionally employed in the aqueous phase. Typical of such antioxidants are sodium sulfite, sodium metabisulfite, sodium bisulfite, sodium thiosulfate, sodium formaldehyde sulfoxylate, acetone sodium metabisulfite, ascorbic acid, isoascorbic acid, thioglycerol, thiosorbitol, thiourea, thioglycolic acid and cysteine hydrochloride The anionic surfactants of the present invention may also be employed with non-ionic surfactants such as polyalkoxyethers, polyalkoxyesters, polyalkoxyamides, fatty acid esters of polyhydric alcohols and fatty alcohols, which minimize the potential of skin irritation caused by the anions. Where desired, the anionic surfactants may also be used in combination with compatible thickening agents such as methylcellulose, tragacanth, sodium alginate, Carbopol 934 (CTFA), bentonite, carboxymethylcellulose and Vee-gum (CTFA). As used above and elsewhere in this specification, (CTFA) indicates that the name used in nomenclature from CTFA Cosmetic Ingredient Directory, 3rd Ed., published by CTFA Association, Inc.

Previously, because of the poor stability of anthralin in dermatological compositions, anthralin containing compositions were seldom, if ever, sold having anthralin concentrations greater than 0.5% by weight. As a result of the improved anthralin stability provided by the present invention, it is now possible to offer highly stable preparations with respect to both anthralin concentration and physical stability of the formulations themselves, such formulations being extremely effective in the topical treatment of psoriasis. Such preparations may have anthralin concentrations of 0.1% to 5.0% by weight or more and are useful for out-patient treatment of psoriasis. Moreover, the results of accelerated high temperature storage stability studies and Arrhenius plots of the data carried out on such formulations enabled projections of stability of both anthralin and the formulations for a period in excess of two years under room temperature storage conditions when stability was assayed by the HPLC method. For purposes of these studies, a retention of less than 90% of the anthralin concentration was deemed to be unacceptable.

To demonstrate the stability of the anthralin-containing products of the present invention, gel compositions containing 1% anthralin by weight (plus a 0.05% by weight overage) were prepared in accordance with the below-depicted Basic Gel Composition set forth in Example 1. All such gel compositions conformed to the Basic Gel Composition and were identical, except for the surfactant employed. In addition to gel compositions prepared with the acid stable, water soluble anionic surfactants of the present invention, gel compositions were prepared using the cationic amine surfactant, Richamate 1655, a product of the Richardson Company, and using triethanolamine stearate, an acid unstable, water soluble anionic surfactant, to demonstrate the lack of anthralin stability in gels containing members of such classes of surfactants. Samples were evaluated under storage conditions at room temperature, 35° C. and 45° C.

EXAMPLE 1

Basic Gel Composition

|  | Grams |
|---|---|
| Part A | |
| Mineral oil (USP) | 164 |
| Propyl gallate | 0.5 |
| BHT | 2.0 |
| Salicylic acid | 2.0 |
| Oleth-2 (CTFA) | 60.0 |
| Isoceteth-20 (CTFA) | 200.0 |
| Ascorbyl palmitate | 1.0 |
| Anthralin | 10.5 |
| Part B | |
| PEG-8 (CTFA) | 50.0 |
| Sorbitol solution (70%) | 20.0 |
| EDTA | 1.0 |
| Sodium bisulfite | 1.0 |
| Ascorbic acid | 10.0 |
| Surfactant | 5.0 |
| Purified water (USP) | q.s. 1000.0 |

The compositions were prepared by admixing the components of part A, and heating to a temperature of 90° C. Agitation was continued until all of the solids were blended. The components of part B were admixed in a separate vessel and heated to 90° C. with continued agitation until all the solids dissolved. Part B was added to part A and the resultant mixture agitated. Agitation was continued for ten minutes, while maintaining the temperature at 90° C. The resulting gel was cooled to packaging temperature and packaged, under an inert gas, in aluminum tubes suitable coated internally so as not to react with the product.

TABLE I

| Surfactant Composition | Anthralin Stability | | | |
|---|---|---|---|---|
| | Storage Temperature | Initial | Equivalent to | |
| | | | 45 | 215 Days |
| A. Sodium lauryl sulfate | RT | 1.05% | 1.027% | 1.09% |
| | 35° C. | 1.05% | * | 0.96% |
| | 45° C. | 1.05% | 1.006% | 0.718% |
| B. Cationic amine (Richamate 1655) | RT | 1.05% | 0.529% | 0.42% |
| | 35° C. | 1.05% | 0% | 0 |
| | 45° C. | 1.05% | 0% | 0 |
| C. Triethanolamine stearate | RT | 1.05% | 0.599% | 0.084% |
| | 35° C. | 1.05% | * | 0 |
| | 45° C. | 1.05% | 0.0034-3% | 0.058% |
| D. Sodium dioctyl sulfosuccinate | RT | 1.05% | 1.045% | 1.07% |
| | 35° C. | 1.05% | * | 0.989% |
| | 45° C. | 1.05% | 0.978% | 0.762% |
| E. Sodium alkyl olefin sulfonate | RT | 1.05% | 1.080% | 1.06% |
| | 35° C. | 1.05% | * | 0.935% |
| | 45° C. | 1.05% | 1.012% | 0.800% |
| F. Sodium cocyl isothionate | RT | 1.05% | 1.076% | 1.09%** |
| | 35° C. | 1.05% | * | 0.958% |
| | 45° C. | 1.05% | 1.026% | 0.833% |
| G. DEA oleth-3-phosphate | RT | 1.05% | 1.091% | 1.09% |
| | 35° C. | 1.05% | * | 1.989% |
| | 45° C. | 1.05% | 1.049% | 0.777% |
| H. Sodium laureth sulfate | RT | 1.05% | 1.089% | 1.094% |
| | 35° C. | 1.05% | * | 0.982% |
| | 45° C. | 1.05% | 1.046% | 0.585% |
| I. Sodium lauryl sulfonate | RT | 1.05% | 1.069% | 1.054% |
| | 35° C. | 1.05% | * | 0.928% |
| | 45° C. | 1.05% | 0.943% | 0.781% |
| J. Sodium octoxynol-3-sulfonate | RT | 1.05% | 1.378% | 0.994% |
| | 35° C. | 1.05% | * | 0.936% |
| | 45° C. | 1.05% | 1.019% | 0.785% |

*determination was not made.
**although the data for 45 days and 215 days indicate that 215 day samples had greater stability than at 45 days, this is attributed to the fact that the analytical method is not sufficiently sensitive to distinguish differences at such low concentrations.

The Basic Gel Composition of Example 1 was employed with higher concentrations of surfactant to demonstrate the upper limits of the range at which the acid stable water soluble anionic surfactants of the present invention may be used. Although still higher concentrations are possible, skin irritation is a limiting factor. The following Table II illustrates the results of this study.

TABLE II

| Composition Surfactant | Storage Temperature | Initial | Equivalent to | |
|---|---|---|---|---|
| | | | 45 days | 215 Days |
| Sodium lauryl sulfate (5%) | RT | 1.05% | 1.068% | 1.09% |
| | 35° C. | 1.05% | —* | —* |
| | 45° C.*** | 1.05% | 0.978% | 0.136% |
| Sodium lauryl sulfate (10%) | RT | 1.05% | 1.01% | 1.03% |
| | 35° C. | 1.05% | —* | 0.932% |
| | 45° C.*** | 1.05% | 0.389% | 0.119% |

***The loss of activity in these samples is believed to be due to leakers in tubes resulting from defective seals and due to loss of viscosity at high temperature.
*Determination was not made.

EXAMPLE 2

A satisfactory gel composition was prepared from the following formula:

|  | Grams |
|---|---|
| Part A | |
| Anthralin (including a 15% overage) | 1.15 |
| Isoceteth-20 (CTFA) | 20.0 |
| Mineral oil (USP) | 16.0 |
| Oleth-2 (CTFA) | 6.0 |
| Salicylic acid | 0.2 |
| Ascorbyl palmitate | 0.1 |
| BHT | 0.1 |
| Propyl gallate | 0.01 |
| Part B | |
| PEG-8 (CTFA) | 5.0 |
| Sorbitol solution (70%) | 2.0 |
| Ascorbic acid | 1.0 |
| Sodium lauryl sulfate | 0.3 |
| Citric acid | 0.1 |
| Sodium bisulfite | 0.05 |
| EDTA | 0.01 |
| Purified water (USP) | q.s. 100.00 |

The gel was prepared by admixing the components of Part A and heating to a temperature of 90° C. Agitation was continued until all of the solids were blended. In a separate vessel, the components of Part B were admixed and heated to 90° C. with continued agitation until all the solids were dissolved. Part B was mixed into Part A and agitation continued for ten minutes while maintaining the temperature at 90° C. The resulting gel was cooled to packaging temperature and packaged in aluminum tubes having a non-reactive internal coating under an inert gas atmosphere.

The composition of Example 2 was subjected to clinical evaluation. In all cases, the same composition was employed, except the anthralin concentration was varied. Clinical studies were carried out by clinical dermatologists having extensive experience in the evaluation of drugs used in the treatment of psoriasis.

These clinical studies demonstrate that gel compositions of the present invention, containing 0.5–2% by weight anthralin, provide especially good results in patients subjected to a once-daily, short-duration therapy of 10 to 20 minutes, over a six-week period of treatment. The patients so treated had psoriasis ranging from localized lesions to lesions over a major portion of their body surface. The patients were evaluated after six weeks. The results of such evaluations are set forth in Table III below and clearly demonstrate the efficacy of 0.5–2% by weight anthralin-containing gel stabilized by means of the present invention.

TABLE III

| Anthralin (%) Treatment | Skin Contact Time (Minutes) | Applied to: | Clinical Response** | No. of Patients | Investigator |
|---|---|---|---|---|---|
| 1% 1st week | 20 | Total | Good | 9 | Dr. H |
| 2% 5 weeks | 10 | body | | | |
| 1% 1st week | 20 | Lesions | Excellent | 10 | Dr. R |
| 2% 5 weeks | 10 | only | | | |
| 0.5% 1st wk. | 20 | Lesions | Excellent | 10 | Dr. E |
| 1% 5 weeks | 10 | only* | | | |
| 0.5% 1st week | 20 | Lesions | Excellent | 20 | Dr. V/E |
| 1% 5 weeks | 10 | only* | | | |
| 0.5% 1st week | 20 | Lesions | Excellent | 11 | Dr. B |
| 1% 5 weeks | 10 | only* | | | |

*Total body application started but degree of irritation on non-involved skin was such that protocol was amended to lesion only-thereafter no problems.
**As used herein, good indicates moderate to significant clearing and excellent indicates significant to complete clearing.

It is worthy of note herein that clinical evaluation of the composition of Example 6 has been initiated. Preliminary results indicate no difference, insofar as clinical efficacy in the short duration treatment of psoriasis between the composition of Example 2 (containing water-soluble antioxidant in the aqueous phase) and the composition of Example 6 (containing no water soluble antioxidant in the aqueous phase).

It should be emphasized herein that the resolution of the anthralin stability problem by the compositions of the present invention facilitates the use of short duration therapy and is extremely beneficial in the treatment of psoriasis.

EXAMPLE 3

A satisfactory cream preparation was prepared from the following formula:

| | Grams |
|---|---|
| Part A | |
| Petrolatum | 200.0 |
| Mineral oil (USP) | 50.0 |
| Steareth-2 (CTFA) | 12.5 |
| Steareth-100 (CTFA) | 2.5 |
| Anthralin | 11.5+ (includes 15% overage) |
| Salicylic acid | 3.5 |
| Propyl gallate | 0.05 |
| BHT | 0.5 |
| Ascorbyl palmitate | 0.5 |
| Part B | |
| Sodium lauryl sulfate | 1.50 |
| Ascorbic acid | 2.0 |
| PEG-8 (CTFA) | 60.0 |
| Dried sodium phosphate | 0.75 |
| EDTA | 0.5 |
| Sorbic acid | 0.5 |
| Xanthan Gum (USP) | 3.25 |
| Purified water (USP) | q.s. 500.00 |

The cream was prepared by admixing the components of Part A and heating to a temperature of 70° C. Agitation was continued until all of the solids were blended. In a separate vessel, the components of Part B were admixed and heated to 70° C. with continued agitation until all the solids were dissolved. Part B was mixed into Part A and agitation continued, while maintaining a temperature of 70° C., until both parts were thoroughly blended. The resulting cream was cooled to packaging temperature and packaged.

EXAMPLE 4

A satisfactory stick composition was prepared from the following formula:

| | Grams |
|---|---|
| Syncrowax HGL-C (Croda) | 45.0 |
| Syncrowax ERL-C (Croda) | 15.0 |
| Petrolatum | 310.0 |
| Mineral oil (USP) | 120.0 |
| Salicylic acid | 0.5 |
| Propyl gallate | 0.05 |
| BHT | 0.25 |
| Ascorbyl palmitate | 0.5 |
| Sodium lauryl sulfate | 2.5 |
| Ascorbic acid | 0.25 |
| Anthralin | 5.75 |
| Purified water (USP) | 4.0 |

The sodium lauryl sulfate and ascorbic acid were dissolved in the water and added to the remaining components which were premixed at 80° C. and then cooled to 75° C. The composition was then poured into molds, allowed to cool and set and packaged.

EXAMPLE 5

A satisfactory ointment composition was prepared from the following formula:

| | Grams |
|---|---|
| Cetostearyl alcohol | 280.0 |
| White soft paraffin | 500.0 |
| Liquid paraffin | 200.0 |
| Sodium lauryl sulfate | 5.0 |
| Salicylic acid | 2.0 |

-continued

|  | Grams |
| --- | --- |
| Ascorbyl palmitate | 1.0 |
| BHA | 0.5 |
| EDTA | 0.05 |
| Ascorbic acid | 0.05 |
| Anthralin | 11.5 |
| Purified water (USP) | 4.00 |

All of the components, with the exception of the anthralin, were vigorously mixed with the water at 75° C. until bubble formation ceased. The anthralin was then added and agitation continued for an additional 30 minutes. The composition was cooled to 55° C. and packaged.

Examples 6 and 7 set forth two additional gel compositions which can be prepared by the method set forth in Example 1 and are extremely stable under extended storage conditions.

EXAMPLE 6

|  | Grams |
| --- | --- |
| Part A |  |
| Anthralin | 11.5 |
| Isoceteth-20 (CTFA) | 200.0 |
| Oleth-2 (CTFA) | 60.0 |
| Mineral oil (USP) | 165.0 |
| Propyl gallate | 0.1 |
| BHT | 1.0 |
| Salicylic acid | 2.0 |
| Ascorbyl palmitate | 1.0 |
| Part B |  |
| PEG-8 (CTFA) | 50.0 |
| Sorbitol (70% solution) | 20.0 |
| EDTA | 0.2 |
| Citric acid | 5.5 |
| Sodium lauryl sulfate | 5.0 |
| Purified water (USP) | q.s. 1000.0 |

EXAMPLE 7

|  | Grams |
| --- | --- |
| Part A |  |
| Anthralin | 10.5 |
| Isoceteth-20 (CTFA) | 200.0 |
| Oleth-2 (CTFA) | 60.0 |
| Mineral oil (USP) | 160.0 |
| Propyl gallate | 0.5 |
| BHT | 2.0 |
| Salicylic acid | 2.0 |
| Ascorbyl palmitate | 1.0 |
| Part B |  |
| PEG-8 (CTFA) | 50.0 |
| Sorbitol (70% solution) | 20.0 |
| Ascorbic acid | 10.0 |
| Sodium bisulfite | 1.0 |
| EDTA | 1.0 |
| Sodium lauryl sulfate | 5.0 |
| Purified water (USP) | q.s. 1000.0 |

Although the anthralin compositions of the present invention are capable of being formulated and used in cream, gel, ointment or stick form, for each of application the cream or gel forms are prepared.

While the present invention has been described by means of the foregoing specification, reference should be had to the appended claims for a definition of the scope of the invention.

What is claimed is:

1. In a pharmaceutically acceptable composition suitable for the topical treatment of psoriasis and containing water and anthralin in amounts sufficient to provide an anti-psoriatic effect, the improvement which comprises providing in said composition the stabilizing combination consisting essentially of an oil soluble antioxidant and an acid stable, water soluble anionic surfactant, said combination being present in an amount sufficient to stabilize the anthralin.

2. The composition according to claim 1 wherein said surfactant is stable at about pH 4 and below.

3. The composition according to claim 1 wherein said surfactant is stable at about pH 3-4.

4. The composition according to claim 1 wherein said surfactant is stable at about pH 3.2.

5. The composition according to claims 2, 3 or 4 further comprising providing said anthralin at a level of about 0.5% by weight to 5.0% by weight and said surfactant is provided in an amount of about 0.05% by weight to about 10% by weight, said percent by weight being based on the entire weight of the composition.

6. The composition according to claims 2, 3, or 4 further comprising providing said anthralin at a level of about 0.1% by weight to about 3.0% by weight and said surfactant at a level of about 0.1% by weight to about 5.0% by weight, said percent by weight being based on the entire weight of the composition.

7. The composition according to claims 2, 3, or 4 further comprising providing said anthralin at a level of about 0.5% by weight to about 2.0% by weight and said surfactant at a level of about 0.3% by weight to about 1.0% by weight, said percent by weight being based on the entire weight of the composition.

8. The composition according to claim 2, 3, or 4 further providing said anthralin at a level of about 0.1% to about 3.0% by weight and said surfactant being selected from the group consisting of alkyl sulfates, alkyl sulfonates, alkyl benzene sulfonates, sulfonyl fatty acids, alkyl phosphates, dioctyl sulfosuccinate, isethionates, alkyl ether sulfates, methyl sarcosines and like non-soap, anionic surfactants, said percent by weight being based on the entire weight of the composition.

9. The composition according to claims 2, 3, or 4 further comprising providing said anthralin at a level of about 0.5% to about 2.0% by weight and said surfactant being selected from the group consisting of alkyl sulfates, sulfonates, alkyl benzene sulfonates, sulfonyl fatty acids, alkyl phosphates, dioctyl sulfosuccinate, isethionates, alkyl ether sulfate, methyl sarcosines and like non-soap, anionic surfactants, said percent by weight being based on the entire weight of the composition.

10. The composition according to claims 2, 3, or 4 further comprising providing said anthralin at a level of about 0.1% to 5.0% by weight and said surfactant at a level of about 0.05% to 10.0% by weight and being selected from the group consisting of alkyl sulfates, sulfonates, alkyl benzene sulfonates, sulfonyl fatty acids, alkyl phosphates, dioctyl sulfosuccinate, isethionates, alkyl ether sulfate, methyl sarcosines and like non-soap, anionic surfactants, said percent by weight being based on the entire weight of the composition.

11. The composition according to claims 2, 3, or 4 further comprising providing said anthralin at a level of about 0.1% to 3.0% by weight and said surfactant at a level of about 0.1% to 5.0% by weight and being selected from the group consisting of alkyl sulfates, sulfonates, alkyl benzene sulfonates, sulfonyl fatty acids, alkyl phosphates, dioctyl sulfosuccinate, isethionates, alkyl ether sulfate, methyl sarcosines and like non-soap, anionic surfactants, said percent by weight being based on the entire weight of the composition.

12. The composition according to claims 2, 3, or 4 further comprising providing said anthralin at a level of about 0.5% to 2.0% by weight and said surfactant at a level of about 0.3% to 1.0% by weight and being selected from the group consisting of alkyl sulfates, sulfonates, alkyl benzene sulfonates, sulfonyl fatty acids, alkyl phosphates, dioctyl sulfosuccinate, isethionates, alkyl ether sulfate, methyl sarcosines and like non-soap, anionic surfactants, said percent by weight being based on the entire weight of the composition.

13. The composition according to claim 10 wherein said surfactant is sodium lauryl sulfate.

14. The composition according to claim 1 wherein said composition is an oil-in-water emulsion and the emulsion contains no antioxidant in the aqueous phase.

15. The composition according to claim 1 wherein the composition is an oil in water or water in oil emulsion and the oil phase contains an amount of an oil soluble antioxidant sufficient to increase anthralin stability.

16. The composition according to claim 15 wherein said composition is an oil in water emulsion.

17. The composition according to claim 15 wherein the composition contains an amount of a water soluble antioxidant in the water phase sufficient to increase anthralin stability.

18. The composition according to claim 1 wherein said anionic surfactant is a mixture of two or more suitable anionic surfactants.

19. A method for increasing the stability of anthralin containing compositions comprising adding to such compositions a stabilizing effective amount of a combination consisting essentially of an oil soluble antioxidant and an acid stable, water soluble, anionic surfactant.

20. The method of claim 19 which further comprises adjusting the pH of said compositions to pH 5.3 or below.

21. The method of claim 19 which further comprises adding a water soluble antioxidant to said composition.

* * * * *